United States Patent [19]

Minagawa et al.

[11] 4,115,476
[45] Sep. 19, 1978

[54] 2,2,6,6-TETRAMETHYL-4-PIPERIDYL CARBONIC ACID ESTERS OF DIHYDRIC ALCOHOLS AND PHENOLS AS STABILIZERS FOR SYNTHETIC POLYMERS

[75] Inventors: Motonobu Minagawa, Kosigaya; Naohiro Kubota; Toshihiro Shibata, both of Urawa, all of Japan

[73] Assignee: Argus Chemical Corporation, Brooklyn, N.Y.

[21] Appl. No.: 794,172

[22] Filed: May 5, 1977

[30] Foreign Application Priority Data

May 20, 1976 [JP] Japan .................................. 51-58221

[51] Int. Cl.$^2$ ...................... C07D 401/12; C08K 5/34; C08K 5/35
[52] U.S. Cl. ...................... 260/880 R; 260/45.89 NP; 260/45.8 NZ; 260/293.63; 260/293.64; 260/293.66
[58] Field of Search ................ 260/45.8 N, 45.8 NZ, 260/293.63, 293.64, 293.66

[56] References Cited
U.S. PATENT DOCUMENTS

| | | | |
|---|---|---|---|
| 2,379,250 | 6/1945 | Muskat et al. | 260/463 |
| 2,746,964 | 5/1956 | Biel | 260/293.63 |
| 2,856,407 | 10/1958 | Biel | 260/293,64 |
| 3,551,520 | 12/1970 | Nehring et al. | 260/463 |
| 3,632,828 | 1/1972 | Frevel et al. | 260/463 |
| 3,640,928 | 2/1972 | Murayama et al. | 260/45.8 N |
| 3,816,373 | 6/1974 | Hoogeboom | 260/463 |
| 3,840,494 | 10/1974 | Murayama et al. | 260/293.63 |
| 3,992,390 | 11/1976 | Holt et al. | 260/45.8 N |
| 4,007,158 | 2/1977 | Murayama et al. | 260/45.8 NZ |
| 4,016,168 | 4/1977 | Murayama et al. | 260/293.66 |

OTHER PUBLICATIONS

Cotter et al., Chemistry and Industry (London), No. 19, 1965, pp. 791-793.

*Primary Examiner*—Donald E. Czaja
*Assistant Examiner*—R. A. White

[57] ABSTRACT

2,2,6,6-Tetramethyl-4-piperidyl carbonic acid esters of dihydric alcohols and phenols are provided, useful as stabilizers for organic polymeric materials, and having the general formula:

$$R_1-O-\underset{\underset{O}{\|}}{C}-\left[-O-Z-O-\underset{\underset{O}{\|}}{C}-\right]_n-O-R_2 \quad I$$

wherein:
$R_1$ and $R_2$ are selected from the group consisting of

[structure: 2,2,6,6-tetramethylpiperidine with $R_3$–N]

[structure with $R_6$, $CH_2$–]

[structure: and $CH_2$–]

[structure]

the $R_1$ and $R_2$ groups can be the same or different;
$R_3$ is selected from the group consisting of hydrogen and O;
$R_6$ is lower alkyl;
$n$ is selected from the group consisting of 1, 2, 3, 4 and 5;
—O—Z—O— is a bivalent aliphatic, cycloaliphatic, aromatic, or mixed aliphatic-aromatic, aliphatic-cycloaliphatic or cycloaliphatic-aromatic radical carrying two hydroxyl groups OH esterified with carbonic acid groups of the piperidyl carbonic acid ester.

33 Claims, No Drawings

2,2,6,6-TETRAMETHYL-4-PIPERIDYL CARBONIC ACID ESTERS OF DIHYDRIC ALCOHOLS AND PHENOLS AS STABILIZERS FOR SYNTHETIC POLYMERS

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

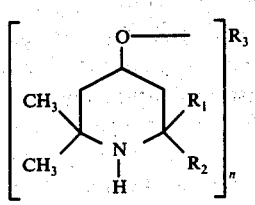

or a salt thereof.

In the above Formula:

$R_1$ and $R_2$ which may be the same or different, each are an alkyl group such as methyl, ethyl, isopropyl or dodecyl, or they form, together with the carbon atom to which they are attached, a saturated alicyclic group such as:

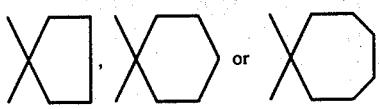

or a group of the formula

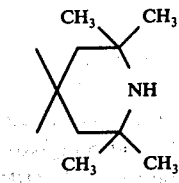

$n$ is an integer of 1 to 3 inclusive: and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al. and others of compounds including a 2,2,6,6-tetrasubstituted-4-piperidyl group attached to a base molecule of varying structures.

Murayama et al. U.S. Pat. No. 3,898,303 patented Aug. 5, 1975 propose piperidino-spiro-hydantoin derivatives having the formula:

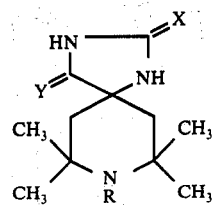

wherein
R represents an alkyl group, an alkenyl group, an alkenoyl group which may be substituted with an aryl group, a hydroxyalkyl group, an alkoxyalkyl group, an alkoxycarbonylalkyl group, an acyloxyalkyl group, a cyanoalkyl group or nitroso group, and X and Y individually represent oxygen atom or sulfur atom.

Murayama et al. in U.S. Pat. No. 3,899,464 patented Aug. 12, 1975 disclose a variation of the piperidino spiro compounds having the formula:

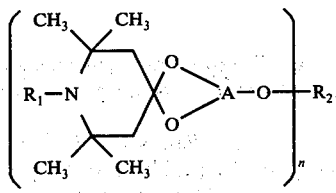

wherein
$R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, $n$ is an integer of 1 to 4;

When $n$ is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

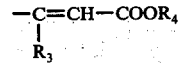

in which
$R_3$ represents hydrogen atom, a lower alkyl group or phenyl group and $R_4$ represents an alkyl group;

when $n$ is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when $n$ is 3, $R_2$ represents an aromatic triacyl group or a trivalent group from an oxoacid; and when $n$ is 4, $R_2$ represents an aromatic tetraacyl group, and A represents a group

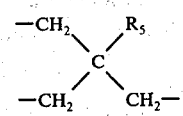

in which $R_3$ represents hydrogen atom or a lower alkyl group or, when $n$ is 1, $R_5$ may represent together with $R_2$ a group

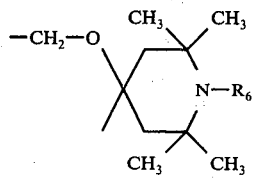

in which $R_6$ represents the same group as defined in $R_1$ and may be the same or different from $R_1$, or a group

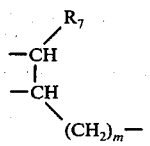

in which $m$ is 1 or 2 and $R_7$ represents hydrogen atom or, when $n$ and $m$ are 1, $R_7$ represents methylene group together with $R_2$.

Murayama et al. U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al. U.S. Pat. No. 3,941,744 patented Mar. 2, 1976, disclose another variation of the piperidino spiro derivatives having the formula:

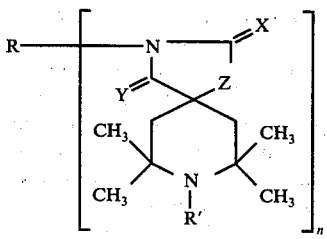

wherein

R' represents an alkyl group, a substituted alkyl group, an acyl group, an alkoxycarbonyl group, a substituted alkoxycarbonyl group, an amino group, a substituted amino group or nitroso group;

X represents oxygen atom or sulfur atom;

Y represents oxygen atom, sulfur atom or a group of the formula =N—R" in which R" is hydrogen atom, an alkyl group or a substituted alkyl group;

Z represents oxygen atom or a group of the formula >N—R''' is hydrogen atom, an alkyl group or a substituted alkyl group;

$n$ is an integer of 1 through 4 inclusive; and

R represents, when $n$ is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when $n$ is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl) group, a dialkylene ether group or a diphenylene ether group, when $n$ is 3, an alkanetriyl group, a tris(acyloxyalkylene) group, an alkane-tris-(oxycarbonylalkyl) group or a group of the group

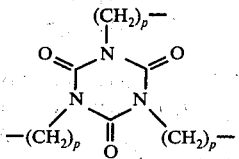

in which $p$ is an integer of 1 through 8 inclusive, and when $n$ is 4, an alkane tetrayl group, a tetrakis-(acyloxyalkylene) group or an alkanetetrakis(oxycarbonylalkyl) group.

Murayama et al. U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

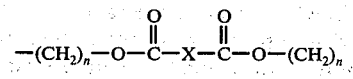

in which $n$ is an integer of 1 or 2 and X is an alkylene group, or o-, m- or p-phenylene group or the carbon atoms of CO groups may be directly joined in the absence of X or a group of the formula:

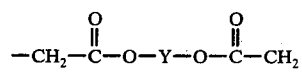

in which

Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperazines and substituted piperazinodiones. The substituted piperazines of U.S. Pat. No. 3,899,491 have the formula:

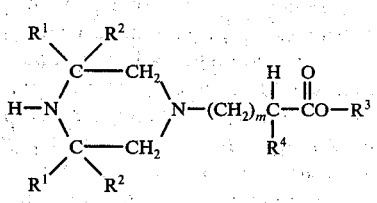

wherein $R^1$ and $R^2$ are methyl or together with the carbon to which they are bound form a mono-cyclic ring system having five or six carbon atoms;

$R^3$ is an alkyl group of from one to twenty atoms;

$R^4$ is hydrogen or methyl, and $m$ is 0 or 1.

The substituted piperazinodiones of U.S. Pat. No. 3,920,659 have the formula:

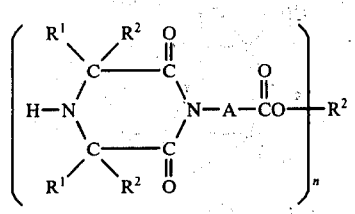

wherein $R^1$ and $R^2$ are independently of each other methyl or ethyl, or together with the carbon to which they are bound form a cyclopentyl or cyclohexyl ring, which is unsubstituted or substituted with a methyl group;

n is an integer of from 1 to 2;

when n is 1, $R^3$ is an alkyl group of from one to 20 carbon atoms;

When n is 2, $R^3$ is an alkylene group of from two to eight carbon atoms; and

A is a straight or branched chain (lower) alkylene group containing from one to six carbon atoms with the limitation that the terminals of said alkylene group bear only hydrogen or one (lower) alkyl group.

Ramey et al. U.S. Pat. No. 3,920,661 patented Nov. 18, 1975 disclose dicarboxylic acids and salts in which one carboxylic acid group is esterified with a 2,2,6,6-tetrasubstituted-4-hydroxy piperidine and having the formula:

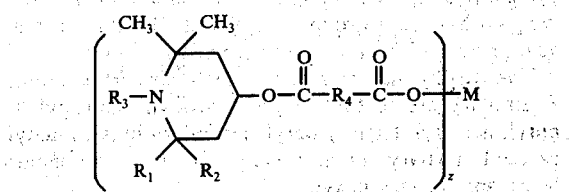

wherein $R_1$ and $R_2$ independently of each other are straight- or branchedchain alkyl having from one to six carbon atoms, or together with the carbon to which they are bound form a cyclopentyl or cyclohexyl ring, which is unsubstituted or substituted with a methyl group;

$R_3$ is hydrogen, alkyl having one to twelve carbon atoms, β-methoxyethyl, alkenyl having three or four carbon atoms, propargyl, benzyl or alkyl-substituted benzyl;

$R_4$ is straight or branched-chain alkylene having five to eight carbon atoms, or the group $(CH_2)_m Y(CH_2)_n$ wherein Y is oxygen or sulfur and m and n independently of each other are an integer from 1 to 3;

M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al. U.S. Pat. No. 3,939,163 patented Feb. 17, 1976 disclose closely similar compounds in which $R_4$ is alkylene having from one to four carbon atoms.

Randell et al. U.S. Pat. No. 3,939,170 patented Feb. 17, 1976 disclose dehydropyridinyl sulphides, sulphoxides and sulphones having the formula:

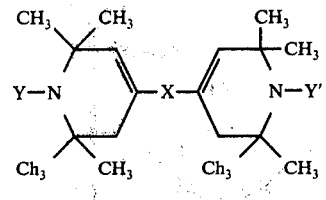

wherein

X is S, SO or $SO_2$ and Y and $Y^1$ are the same or different and each is H, OH, O— or a straight- or branched alkyl residue having from one to four carbon atoms, and salts thereof when Y and $Y^1$ are other than O—

Randell et al. in published patent application Ser. No. B408,123 published Apr. 13, 1976 disclose substituted piperidine-4-ols having the formula:

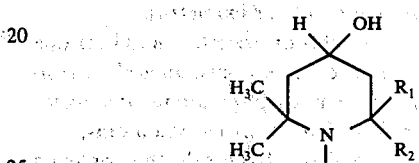

wherein $R_1$ and $R_2$ are the same or different and each is a straight- or branched alkyl residue having from one to twelve carbon atoms, or $R_1$ and $R_2$, together with the carbon atom to which they are attached, form a cycloakyl residue having from five to twelve carbon atoms or the group:

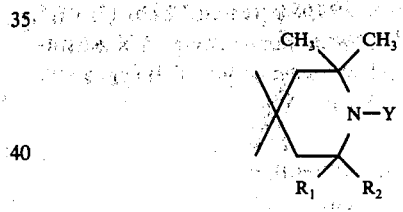

wherein $R_1$ and $R_2$ have their previous significance and Y is a straight- or branched alkyl reside having from one to twenty carbon atoms, an alkenyl or alkynyl residue having from three to twenty carbon atoms, an aralkyl residue having from seven to twelve carbon atoms or the group $—CH_2X$ wherein X is the group

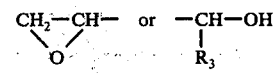

wherein $R_3$ is hydrogen, a methyl or phenyl residue, the group

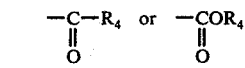

wherein $R_4$ is an alkyl residue having from 1 to 20 carbon atoms. Cook U.S. Pat. No. 3,929,804 patented Dec. 30, 1975 discloses 4-piperidine acetamide compounds having the formula:

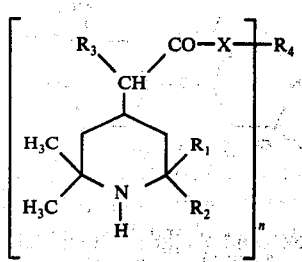

wherein $R_1$ and $R_2$ are the same or different and each is a straight- or branched alkyl residue having from one to 12 carbon atoms, or $R_1$ and $R_2$, together with the carbon atom to which they are attached form a cycloalkyl group having from five to 12 carbon atoms;

$R_3$ is hydrogen, a straight- or branched alkyl residue having from one to four carbon atoms, an aralkyl residue having from seven to nine carbon atoms or a cycloalkyl group having from five or six carbon atoms;

$R_4$ is a metal ion or a hydrocarbyl residue having from two to twenty carbon atoms and being either unsubstituted or substituted by halogen or interrupted by one or more oxygen or sulphur atoms;

X is —O—, —S—, or >$NR_5$, wherein $R_5$ has the same significance as $R_3$; and $n$ is 2, 3 or 4;

as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

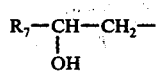

wherein $R_7$ is hydrogen, alkyl or phenyl.

In accordance with the instant invention, 2,2,6,6-tetramethyl-4-piperidyl carbonic acid esters of dihydric alcohols and phenols are provided, useful as stabilizers for organic polymeric materials, having the general formula:

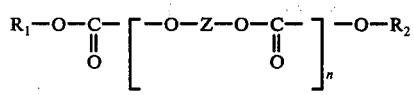

wherein:

$R_1$ and $R_2$ are selected from the group consisting of

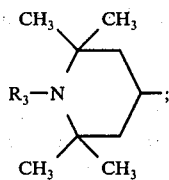

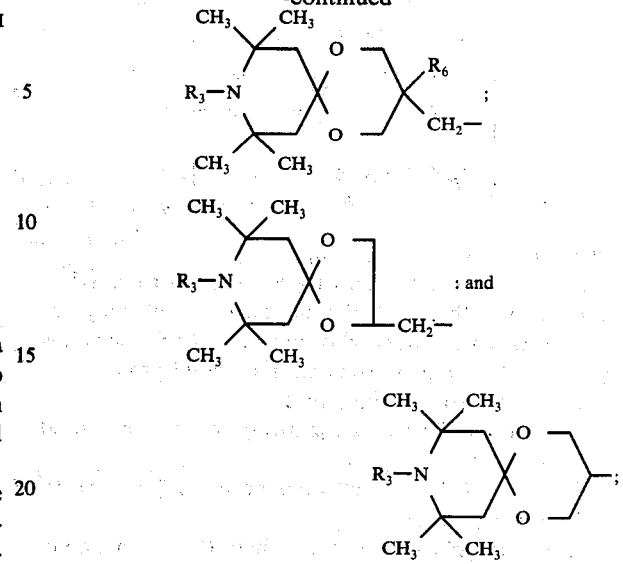

the $r_1$ and $r_2$ groups can be the same or different;

$R_3$ is selected from the group consisting of hydrogen and O;

$R_6$ is lower alkyl;

$n$ is selected from the group consisting of 1, 2, 3, 4 and 5;

—O—Z—O— is a bivalent aliphatic, cycloaliphatic, aromatic, or mixed aliphatic-aromatic, aliphatic-cycloaliphatic or cycloaliphatic-aromatic radical carrying two hydroxyl groups OH esterified with carbonic acid groups of the piperidyl carbonic acid ester.

The $R_6$ alkyl has from one to about six carbon atoms. Exemplary are methyl, ethyl, n-propyl, isopropyl, n-butyl, isobutyl, tertiary butyl, secondary butyl, n-amyl, isoamyl, tertiary amyl, n-hexyl, isohexyl, secondary hexyl and tertiary hexyl.

The Z radical has from two to about twenty-four carbon atoms in an open chain or cyclic saturated or ethylenically unsaturated structure, or mixed open chain substituted cyclic saturated or ethylenically unsaturated structure. Exemplary are ethylene, propylene, butylene, pentylene, hexylene, octylene, nonylene, decylene, dodecylene, tetradecylene, hexadecylene, octadecylene, cyclopentylene, cyclohexylene, cycloheptylene, ethylidene, 2,2,6,6-tetraethylene cyclohexylene, 1-hydroxyl-2,2,6,6-tetraethylene cyclohexylene, and can include ether —O—and thioether—S—linking groups between alkylene groups as in polyoxyalkylene and polythioalkylene groups having from one to about five oxy or thio groups and from two to about six alkylene groups having from two to about six carbon atoms.

The Z arylene have from six to 24 carbon atoms and include phenylene, naphthylene and phenanthrylene.

The mixed Z alkcycloalkylene and cycloalkylene have from about four to about twenty-four carbon atoms, and include methylcyclohexylene, dibutyl cyclohexylene, ethyl cyclopentylene, trimethyl cyclobutylene, cyclopentane dimethylene; cycloheptane dimethylene; cyclohexane diemthylene; cyclohexane dipropylene; cyclopentane diethylene; and cyclohexane dibutylene.

The Z arylene and alkarylene have from seven to about twenty-four carbon atoms, and include benzene dimethylene; xylylene; 2,2-diphenyl isopropylidene;

phenethylene, ethylphenylene, propylphenylene, butylphenylene, tolylene, phenpropylene, phenbutylene, naphthethylene and ethylnaphthylene.

Exemplary dihydric alcohols and phenols from which the Z radical is derived include ethylene glycol, diethylene glycol, triethylene glycol, propylene glycol, butylene glycol, pentanediol, hexanediol, neopentylglycol, thiodiethylene glycol, cyclohexane dimethanol, phenyldimethanol, hydrogenated Bisphenol A, cyclohexanediol hydroquinone, 2,5-di-t-butylhydroquinone, 2,3,6-trimethylhydroquinone, 2-methylresorcinol; 2,6-di-t-butylresorcinol; 2,2'-methylene-bis-(4-methyl-6-t-butylphenol); 2,2'-methylene-bis-(4-methyl-6(α-methylcyclohexyl)phenol); 2,2'-n-butylidene-bis-(4,6-di-methylphenol), bis-1,1-(2'hydroxy-3',5'-di-methylphenyl)-3,5,5-trimethylhexane; 2,2' cyclohexylidene bis-(4-ethyl-6-t-butylphenol); 2,2'-isopropylbenzylidene-bis-(4-ethyl-6-t-butylphenol); 2,2'-thio-bis-(4-t-butyl-6-methylphenol); 2,2' thio-bis-(4-methyl-6-t-butylphenol); 2,2'-thio-bis(4,6-di-t-butylphenol); 4,4'-bis(2,6-di-t-butylphenol); 4,4'-bis-(2,6-di-t-butylphenol); 4,4'-methylene-bis(2-methyl-6-t-butylphenol); 4,4'-methylene-bis-(2,6-di-t-butylphenol); Bisphenol A, 4,4'-isopropylidenebis-(2-phenylethylphenol); 4,4'-n-butylidene-bis-(3-methyl-6-t-butylphenol); 4,4'cyclohexylidene-bis-(2-t-butylphenol); 4,4'-cyclohexylidene-bis-(2-cyclohexylphenol); 4,4'-benzylidene-bis-(2-t-butyl-5-methylphenol); 4,4'-oxo-bis-(3-methyl-6-isopropylphenol); 4,4'-thio-bis-(3-methyl-6-t-butylphenol); 4,4'-sulfo-bis-(3-methyl-6-t-butylphenol); and bis-(2-methyl-4-hydroxy-5-t-butylbenzyl) sulfide.

The following compounds are exemplary:

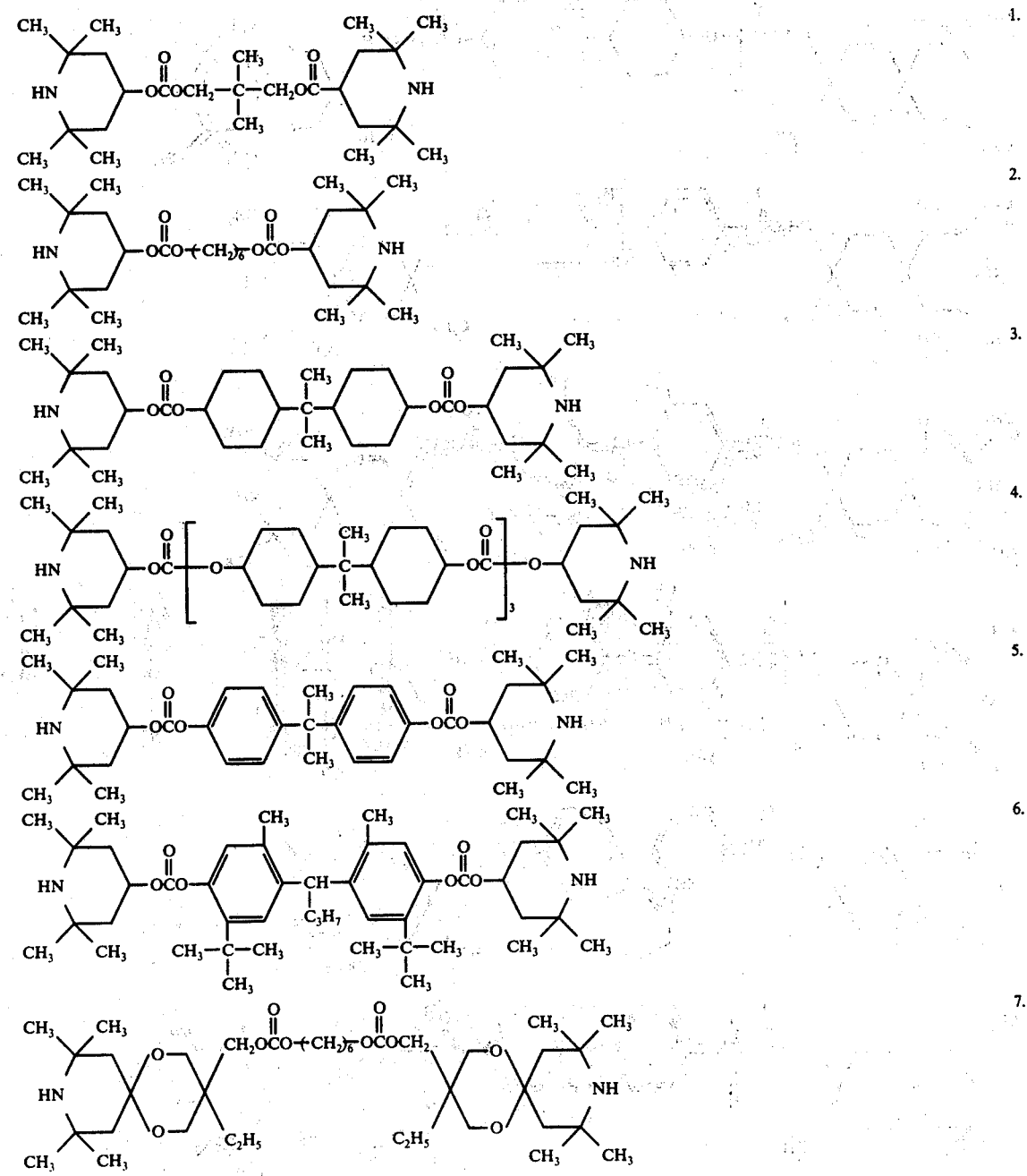

-continued
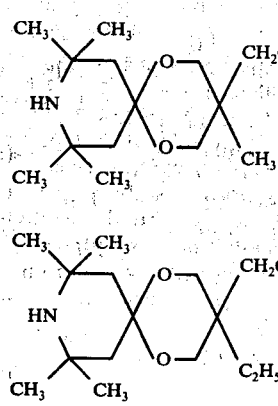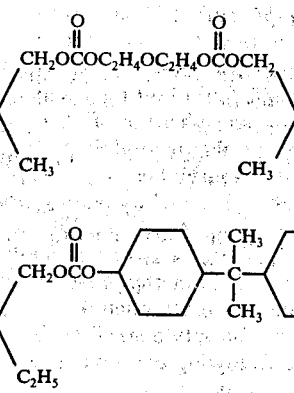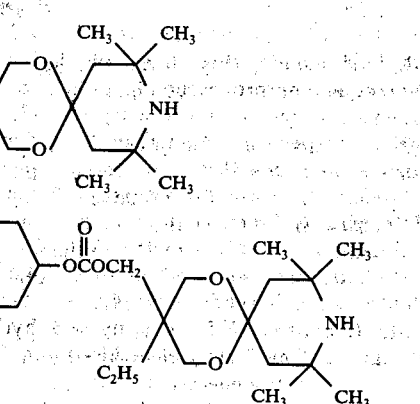
8.
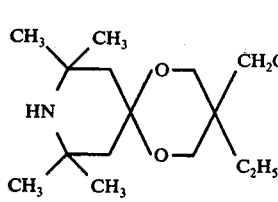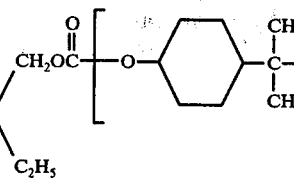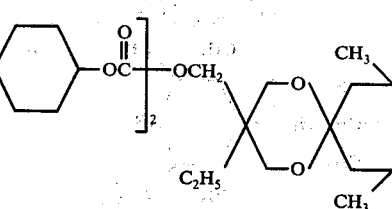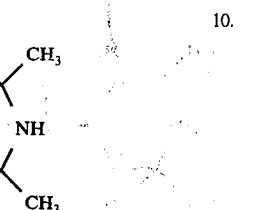
9.
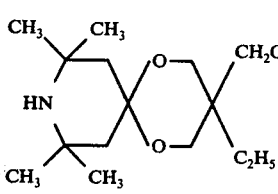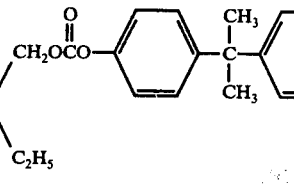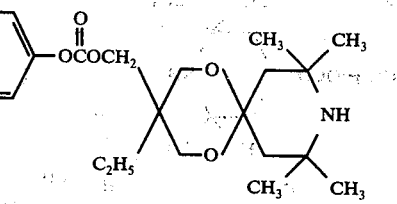
10.
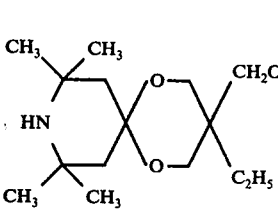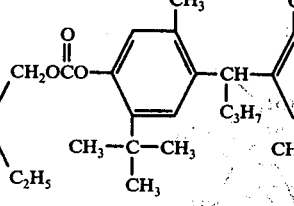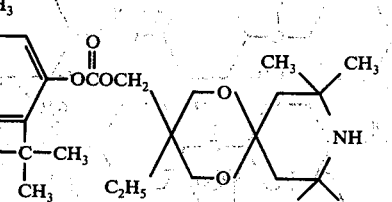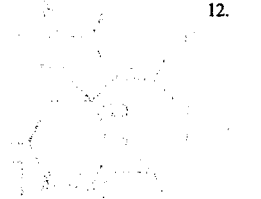
11.
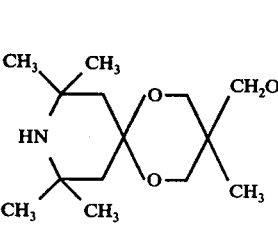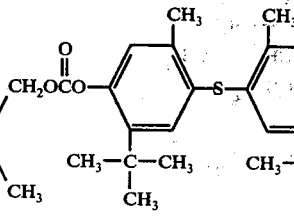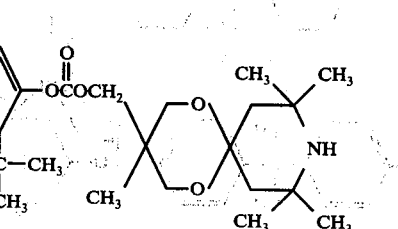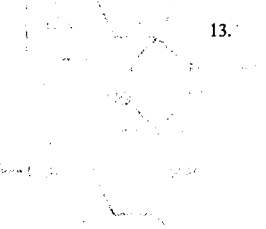
12.
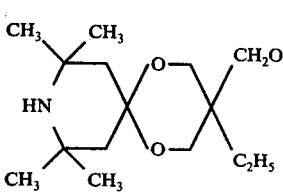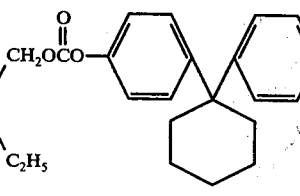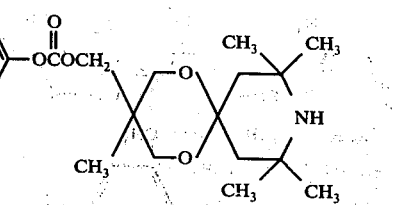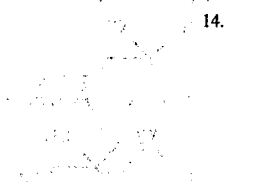
13.
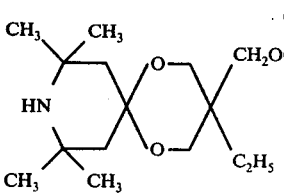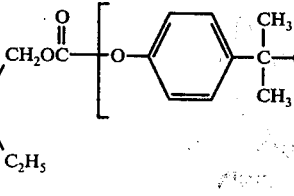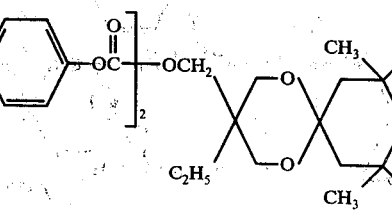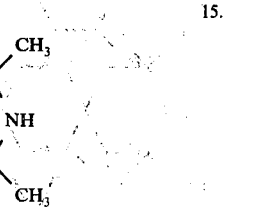
14.
15.

-continued
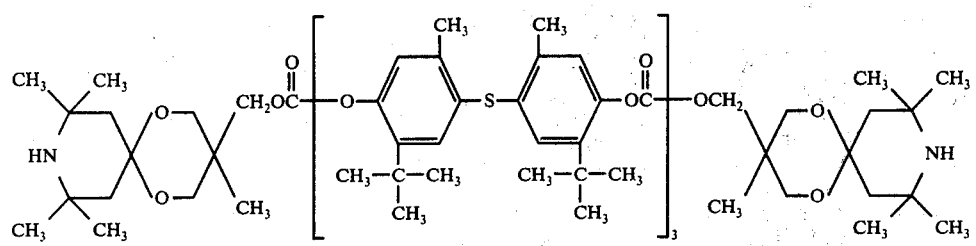
16.
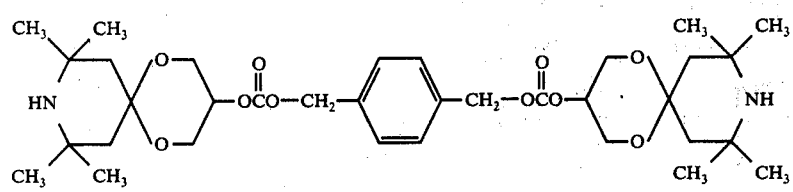
17.
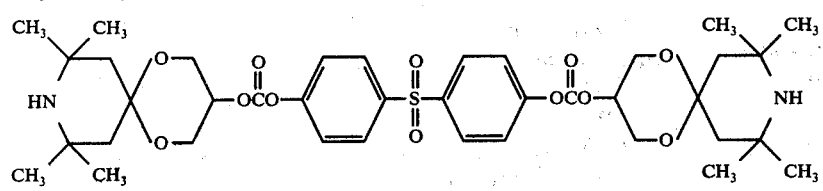
18.
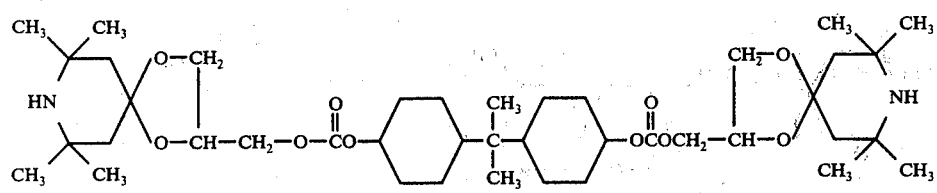
19.
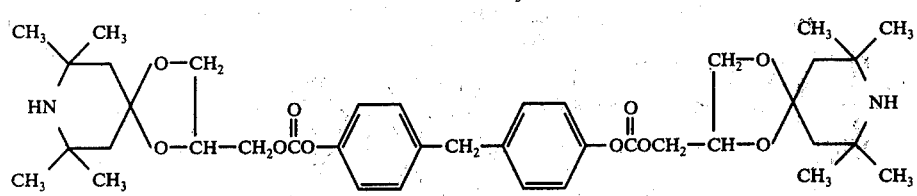
20.
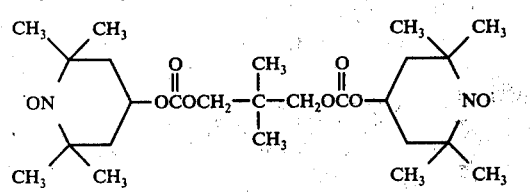
21.
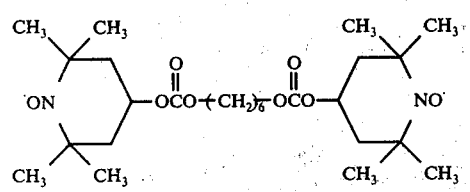
22.
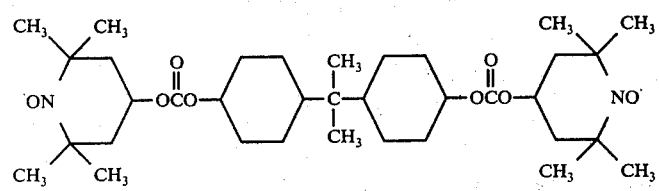
23.
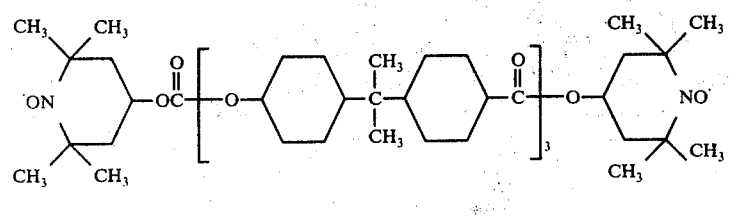
24.

-continued
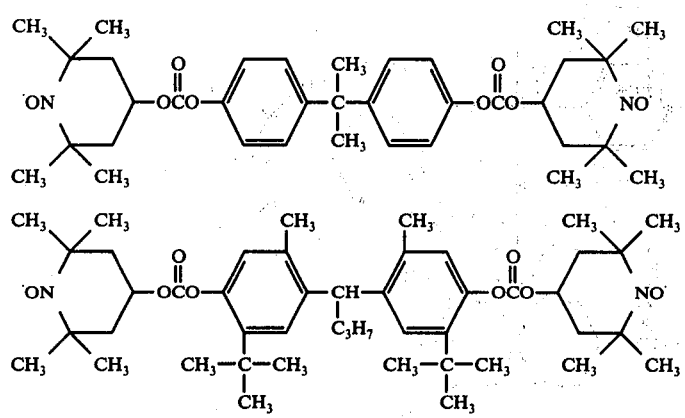
25.
26.
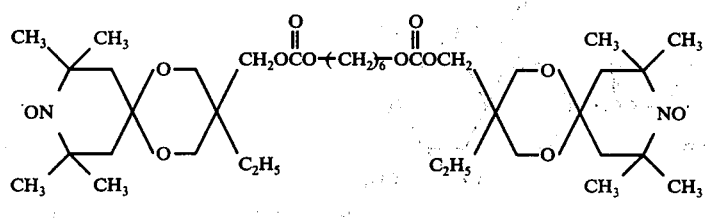
27.
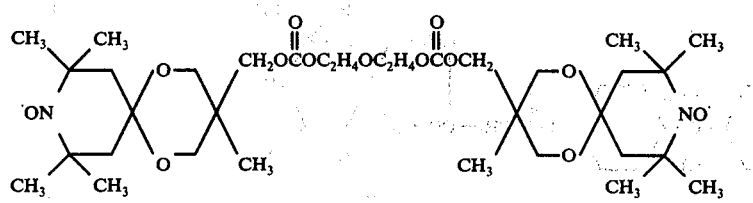
28.
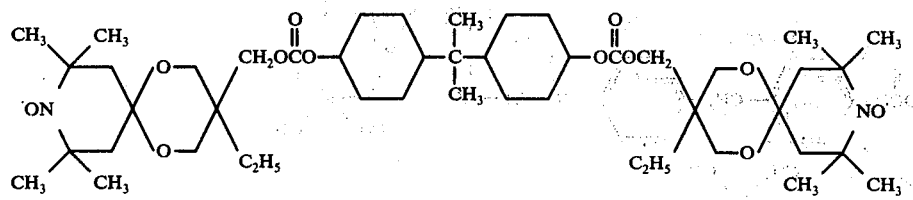
29.
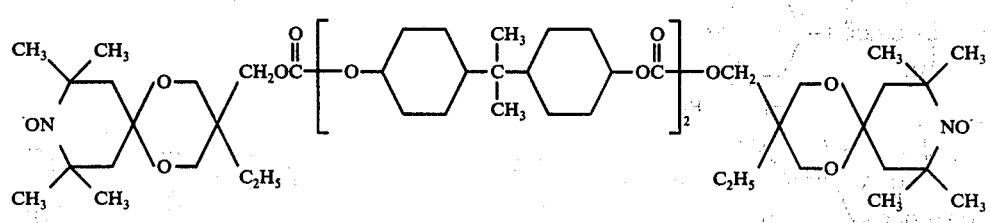
30.
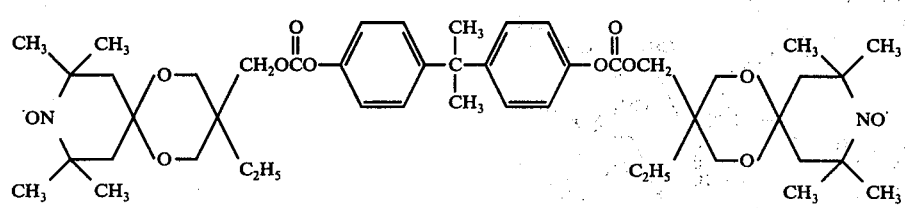
31.
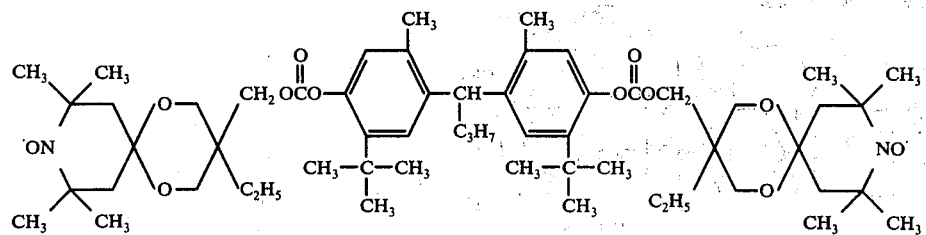
32.

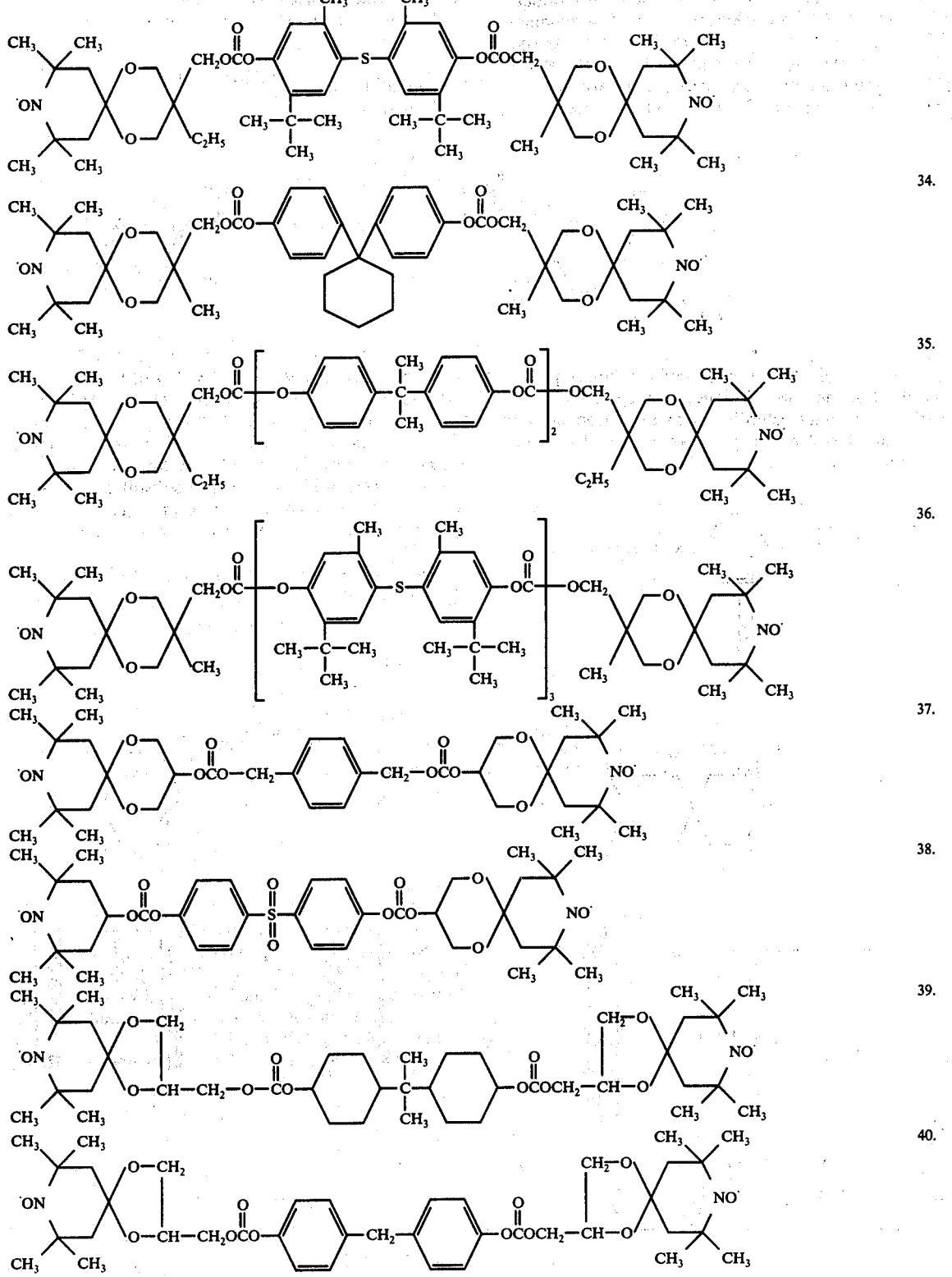

The compounds in accordance with the invention are readily prepared using conventional procedures. The starting materials are either available or readily syntehsized without difficulty. The corresponding 2,2,6,6-tetrasubstituted-4-hydroxy piperidine is used as a starting material for the 2,2,6,6-tetrasubstituted-4-piperidyl groups $R_1$, $R_2$. This is reacted optionally in the presence of an organic solvent, diphenyl carbonate, an alkaline catalyst and the corresponding dihydric alcohol or phenol. The alkaline catalyst can be any alkaline catalyst conventionally employed for transesterification reactions, such as an alkali or alkaline earth metal oxide or hydroxide or an alkaline salt of an alkali or alkaline earth metal, such as carbonate, or hydride, or alcoholate. Sodium is quite satisfactory, and so are sodium hydroxide, lithium carbonate, sodium carbonate, potassium carbonate, lithium hydroxide, potassium hydroxide, sodium hydride, lithium hydride, potassium hydride, calcium hydride, the oxides and hydroxides of calcium, strontium and barium, and the alcoholates, usually of methyl, ethyl or isopropyl alcohol, or phenolates of all of these metals. The hydroxy group of the piperidine becomes esterified with the carbonate and alcohol or phenol forming the 4-piperidinyl carbonic acid ester of the invention:

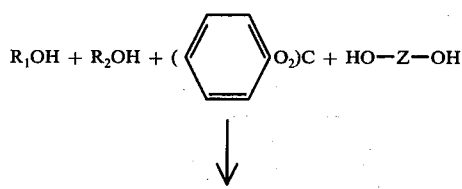
↓

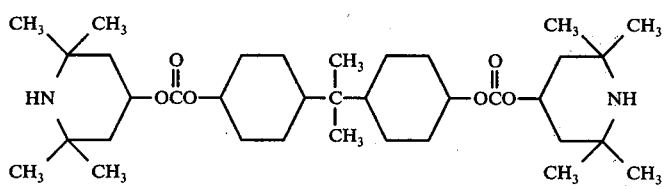

EXAMPLE I

Preparation of

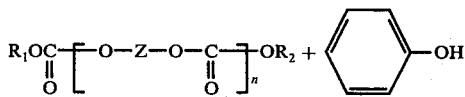

2,2,6,6-tetramethyl-4-hydroxy-piperidine 7.8 g (0.05 mole), diphenylcarbonate 10.7 g (0.05 mole), hydrogenated Bisphenol A 6.0 g (0.025 mole) and potassium carbonate 0.02 g were reacted at 140° C. for 3 hours under nitrogen. Then, phenol was distilled off at up to 170° C. maximum temperature for 1.5 hours under reduced pressure. A colorless glassy solid was obtained with a softening temperature of 45°–50° C.

The product was shown by analysis to have the formula shown above.

EXAMPLE II

Preparation of

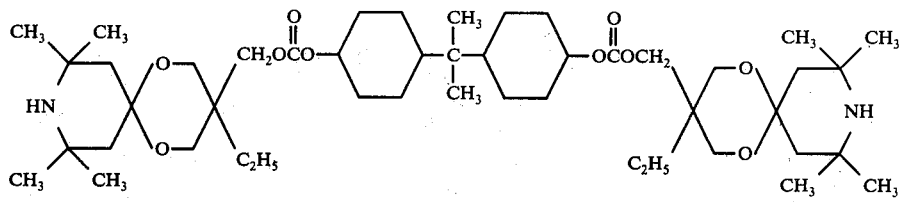

9-aza-3-ethyl-3-hydroxymethyl-8,8,10,10-tetramethyl-1,5-di-oxaspiro (5.5) undecane 13.5 g (0.05 mole), diphenylcarbonate 10.7 g (0.05 mole), hydrogenated Bisphenol A 6.0 g (0.025 mole) and potassium carbonate 0.03 g were reacted at 130° C. for 3 hours under a nitrogen atmosphere. Then, phenol was distilled off at up to 160° C. for 1 hour under reduced pressure. A colorless glass solid was obtained with a softening temperature of 51°–57° C.

The product was shown by analysis to have the formula shown above.

EXAMPLE III

Preparation of

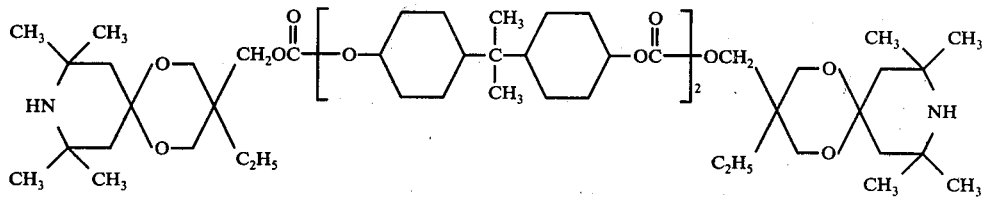

9-aza-3-ethyl-3-hydroxymethyl-8,8,10,10-tetramethyl-1,5-di-oxa spiro (5.5) undecane 5.4 g (0.02 mole), diphenylcarbonate 6.4 g (0.03 mole), hydrogenated Bisphenol A 4.8 g (0.02 mole) and potassium carbonate 0.02 g were reacted at 130° C. for 3 hours under a nitrogen atmosphere. Then, phenol was distilled off at up to 160° C. for 2 hours under reduced pressure. A colorless glassy solid was obtained with a softening temperature of 52°–59° C.

The product was shown by analysis to have the formula shown above.

EXAMPLE IV

Preparation of

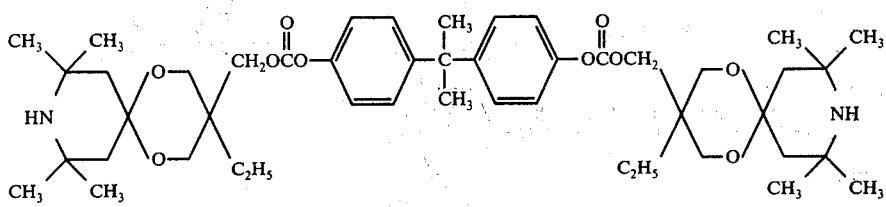

9-aza-3-ethyl-3-hydroxymethyl-8,8,10,10-tetramethyl-1,5-di-oxa spiro (5.5) undecane 13.5 g (0.05 mole), diphenylcarbonate 10.7 g (0.05 mole), Bisphenol A 5.7 g (0.025 mole) and potassium carbonate 0.03 g were reacted at 130° C. for 3 hours under a nitrogen atmosphere. Then, phenol was distilled off at up to 160° C. for 1 hour under reduced pressure. A very slightly yellow glass solid was obtained, with a softening temperature of 43°–51° C.

Analysis showed the product corresponded to the formula shown above.

The 2,2,6,6-tetrasubstituted-4-piperidyl carbonic acid esters of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylene-pentene copolymers, ethylenevinyl acetate copolymers, styrene-butadiene copolymers, acrylonitrile-styrenebutadiene copolymers, synthetic rubbers of all types, such as polychloroprene; polyvinyl halides, including polyvinyl chloride homopolymer; polyvinylidene chloride; and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncarprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The piperidyl carbonic acid esters of the invention can be used as a stabilizer in an amount within the range from about 0.01 to about 5 parts by weight, preferably from 0.05 to 3 parts by weight, per 100 parts by weight of resin.

The stabilizers of the invention can be employed as the sole stabilizer or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, orgaic phosphites, phenolic and thiophenolic antioxidants, and the higher fatty alcohol esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile-butadiene-styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flameproofing agents, pigments and fillers, can be employed.

The following Examples in the opinion of the inventors represent preferred embodiments of synthetic resin compositions in accordance with the invention

EXAMPLES 1 to 7

A group of polyvinyl chloride resin compositions was prepared having the following formulation:

| Ingredient | Parts by Weight |
| --- | --- |
| Polyvinyl chloride | 100 |
| Dioctylphthalate | 48 |
| Epoxidized soybean oil | 2.0 |
| Tris nonyl phenyl phosphite | 0.2 |
| Ca stearate | 1.0 |
| Zn stearate | 0.1 |
| Stabilizer as shown in Table I | 0.2 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light.

This test was repeated for a total of seven stabilizers in accordance with the invention, having the formulae indicated in Table I, in comparison with two controls, 2-hydroxy-4-methoxy benzophenone, and bis (2,2,6,6-tetramethyl-4-piperidinyl) carbonate. The following results were obtained:

TABLE I

| Example No. | Stabilizer | Hours to Failure | Color |
| --- | --- | --- | --- |
| Control 1 | 2-hydroxy-4-methoxy benzophenone | 330 | Light yellow |
| Control 2 | Bis (2,2,6,6-tetramethyl-4-piperidinyl) carbonate | 205 | Colorless |

TABLE I-continued

| Example No. | Stabilizer | Hours to Failure | Color |
|---|---|---|---|
| 1. | [structure] | 505 | Colorless |
| 2. | [structure] | 510 | Colorless |
| 3. | [structure] | 535 | Colorless |
| 4. | [structure] | 510 | Colorless |
| 5. | [structure] | 485 | Colorless |
| 6. | [structure] | 460 | Colorless |
| 7. | [structure] | 475 | Colorless |

It is apparent that each of the stabilizers in accordance with the invention is far superior to the Controls, which are conventional ultraviolet light stabilizers for polyvinyl chloride.

EXAMPLES 8 to 15

Polypropylene compositions were prepared using stabilizers of the invention and two of the prior art, and having the following formulation:

| Ingredient | Parts by Weight |
|---|---|
| Polypropylene | 100 |
| Dilauryl thiodipropionate | 0.3 |
| Stearyl β-3,5-di-tert-butyl-4-hydroxyphenyl propionate | 0.1 |

-continued

| Ingredient | Parts by Weight |
|---|---|
| Distearyl pentaerythritol diphosphite | 0.1 |
| Stabilizer as shown in Table II | 0.3 |

The compositions were thoroughly blended in a Brabender Plastograph, and then compression-molded to form sheets 0.5 mm thick. Pieces 2.5 cm square were cut off from the sheets and exposed to a carbon arc in a Weather-O-Meter for 350 hours. Elongation before and after 350 hours exposure was determined in comparison with two controls, 2-(2'-hydroxy-5'-chlorophenyl) benzotriazole and bis (9-aza-8,8,10,10-tetramethyl-3-ethyl-1,5-dioxaspiro (5,5)-3-undecyl methyl sebacate, and the percent of retention of elongation is shown in Table II.

TABLE II

| Ex. No. | Stabilizer | % Elongation Retention |
|---|---|---|
| 1 | 2(2'-hydroxy-5'-chlorophenyl) benzotriazole | 21.8 |
| Control 2 | Bis (9-aza-8,8,10,10-tetramethyl-3-ethyl-1,5-dioxaspiro (5,5)-3-undecylmethyl sebacate | 23.5 |
| 8. | [structure] | 58.3 |
| 9. | [structure] | 60.2 |
| 10. | [structure] | 60.6 |
| 11. | [structure] | 63.7 |
| 12. | [structure] | 59.8 |
| 13. | [structure] | 61.5 |
| 14. | [structure] | 57.2 |

TABLE II-continued

| Ex. No. | Stabilizer | % Elongation Retention |
|---|---|---|
| 15. | [structure: bis(2,2,6,6-tetramethyl-piperidinyl) derivative with cyclohexyl-C(CH₃)₂-cyclohexyl central linker and -O-CH₂-CH(-O-)-CH₂-O-CO- ester linkages] | 58.8 |

It is apparent from the above results that the compounds of the invention are superior stabilizers in enhancing the resistance of the polypropylene polymer composition to deterioration in the presence of ultraviolet light.

EXAMPLES 16 to 23

Ethylene-vinyl acetate copolymer compositions were prepared using stabilizers of the invention and two of the prior art, and having the following formulation:

| Ingredient | Parts by Weight |
|---|---|
| Ethylene-vinylacetate copolymer | 100 |
| 2,6-di-t-butyl-p-cresol | 0.1 |
| Ca-stearate | 0.1 |
| Zn-stearate | 0.1 |
| Diisodecylphenylphosphite | 0.2 |
| Stabilizer as shown in Table III | 0.3 |

The stabilizer was blended with the polymer on a two-roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results in comparison with two controls, 2-hydroxy-4-methoxy benzophenone and bis (2,2,6,6-tetramethyl-4-piperidinyl) adipate, are given in Table III as % retention of the initially determined tensile strength:

TABLE III

| Example No. | Stabilizer | % Retention of Tensile Strength After 500 Hours |
|---|---|---|
| Control 1 | 2-hydroxy-4-methoxy benzophenone | 70 |
| Control 2 | Bis(2,2,6,6-tetramethyl-4-piperidinyl)adipate | 73 |
| 16. | [bis(2,2,6,6-tetramethyl-4-piperidinyl) sebacate-like structure: HN-piperidinyl-OCO-(CH₂)₆-OCO-piperidinyl-NH] | 84 |
| 17. | [bis(2,2,6,6-tetramethyl-4-piperidinyl) structure with -OCO-[O-cyclohexyl-C(CH₃)₂-cyclohexyl-OC-O-]₃ central linker] | 82 |
| 18. | [bis(2,2,6,6-tetramethyl-4-piperidinyl) structure with -OCO-phenyl-C(CH₃)₂-phenyl-OC- central linker] | 85 |
| 19. | [bis-piperidinyl structure with CH₂OCOC₂H₄OC₂H₄OCOCH₂ central linker and dioxaspiro piperidine rings] | 82 |

TABLE III-continued

| Example No. | Stabilizer | % Retention of Tensile Strength After 500 Hours |
|---|---|---|
| 20. | 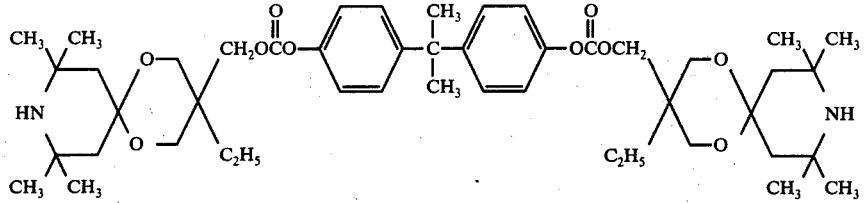 | 86 |
| 21. | 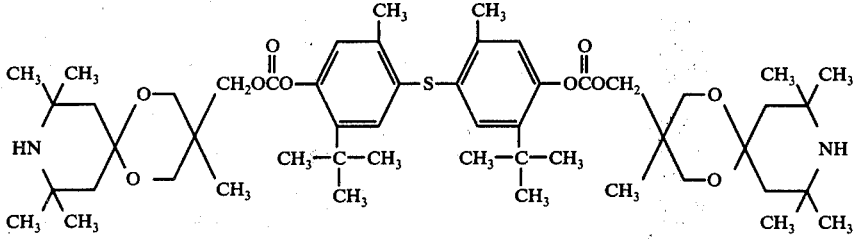 | 83 |
| 22. | 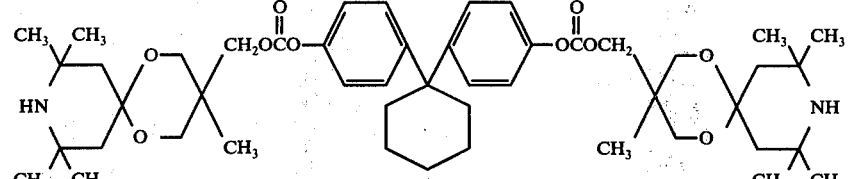 | 84 |
| 23. | 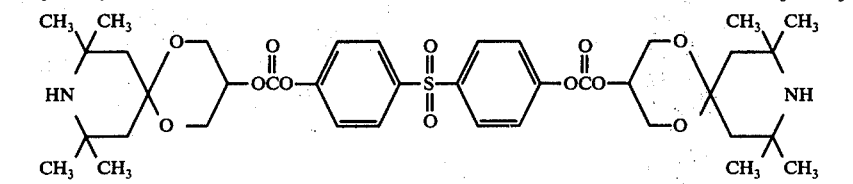 | 80 |

It is apparent from the results that the stabilizer compositions in accordance with the invention are superior to 2-hydroxy-4-methoxy benzophenone and bis (2,2,6,6-tetramethyl-4-piperidinyl) adipate in enhancing the resistance of the ethylene-vinyl acetate copolymer to deterioration in the presence of ultraviolet light.

EXAMPLES 24 to 30

High density polyethylene compositions were prepared using the stabilizers of the invention and two of the prior art, and having the following formulation:

| Ingredient | Parts by Weight |
|---|---|
| High-density polyethylene | 100 |
| Ca-stearate | 1.0 |
| Tetrakis methylene-3-(3,5-di-t-butyl-4-hydroxyphenyl) propionate methane | 0.1 |
| Distearylthiodipropionate | 0.3 |
| Stabilizer as shown in Table IV | 0.3 |

The stabilizer was blended with the polymer on a two-roll mill and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV:

TABLE IV

| Ex.No. | Stabilizer | Hours to Failure |
|---|---|---|
| Control 1 | 2,4-di-t-butylphenyl-3,5-di-5-butyl-4-hydroxybenzoate | 560 |
| Control 2 | 2,2,6,6-tetramethyl-4-piperidinyl benzoate | 530 |

TABLE IV-continued

| Ex.No. | Stabilizer | Hours to Failure |
|---|---|---|
| 24. | 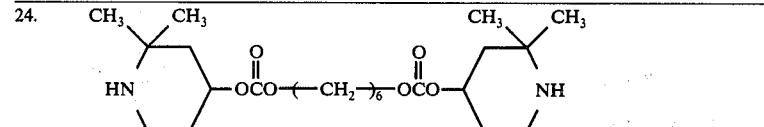 | 1,500 |
| 25. | 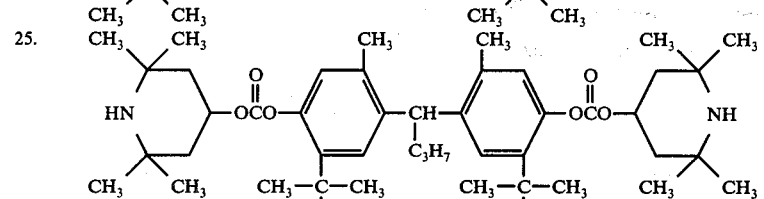 | 1,610 |
| 26. | 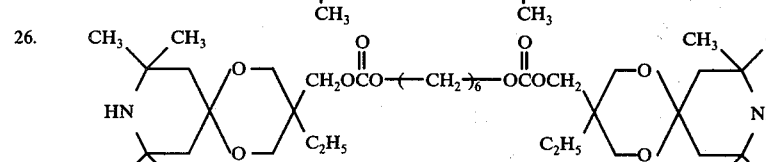 | 1,490 |
| 27. | 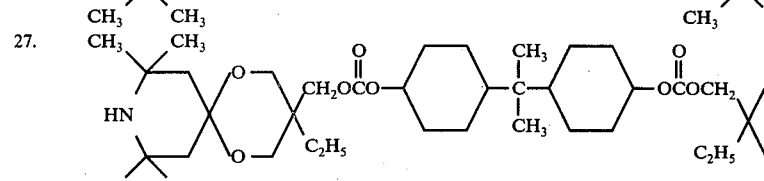 | 1,670 |
| 28. | 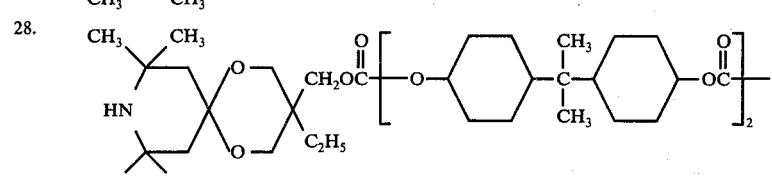 | 1,340 |
| 29. | 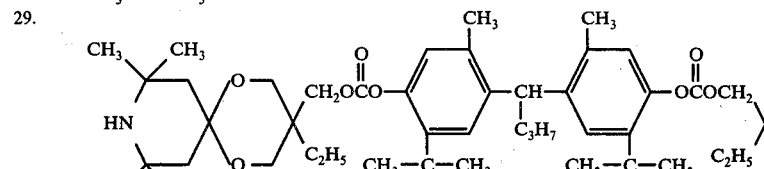 | 1,580 |
| 30. | 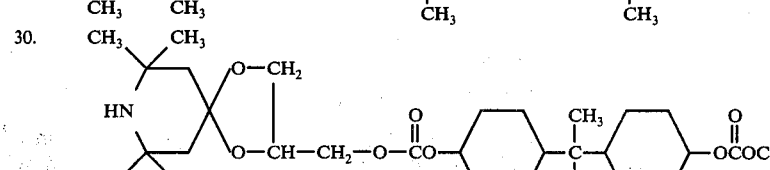 | 1,420 |

The stabilizers of the invention are clearly superior to the controls in enhancing resistance of the polyethylene to degradation under ultraviolet light.

EXAMPLES 31 to 35

Five acrylonitrile-butadiene-styrene terpolymer resin compositions were prepared using stabilizers of the invention and two of the prior art, and having the following formulations:

| Ingredient | Parts by Weight |
|---|---|
| Acrylonitrile-butadiene-styrene terpolymer | 100 |
| 4,4'-butylidene-bis(2-tert-butyl-m-cresol) | 0.1 |
| Stabilizer as shown in Table V | 0.3 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| Ex. No. | Stabilizer | % Tensile Strength Retained |
|---|---|---|
| Control 1 | 2(2'-hydroxy-5'-chlorophenyl)benzotriazole | 62 |
| Control 2 | Phenylsalicylate | 41 |
| 31. | 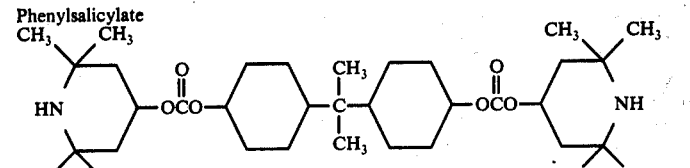 | 91 |
| 32. | 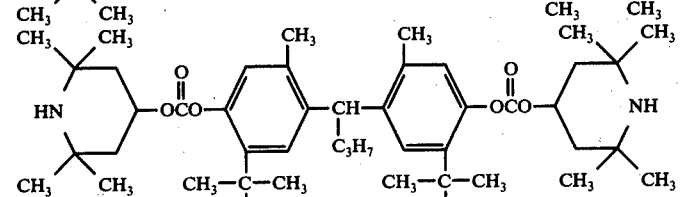 | 89 |
| 33. | 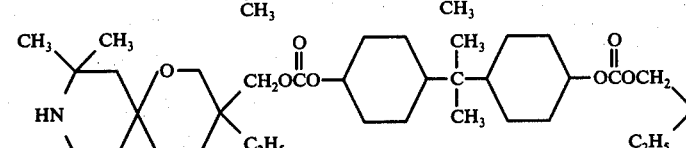 | 93 |
| 34. | 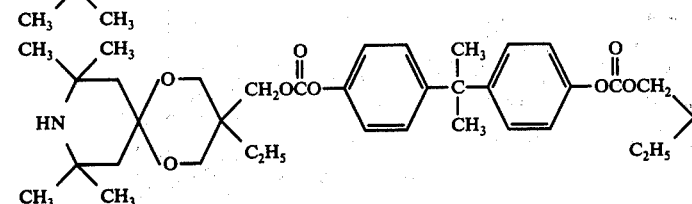 | 90 |
| 35. | 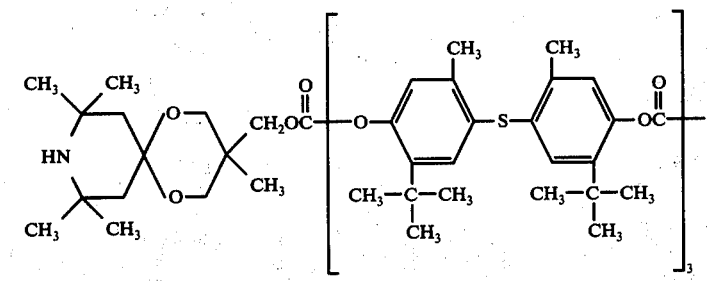 | 87 |

It is apparent from the data that the stabilizers of the invention are superior to the 2(2'-hydroxy-5'-chlorophenyl benzotriazole and phenol salicylate of the prior art.

EXAMPLES 36 to 40

Polybutylene terephthalate resin formulations were prepared having the following composition:

| Ingredient | Parts by Weight |
|---|---|
| Polybutylene terephthalate | 100 |
| 1,3,5-trimethyl-2,4,6-tris (3,5-di-t-butyl-4-hydroxybenzyl) benzene | 0.1 |
| Stabilizer as shown in Table VI | 0.2 |

The compositions were extruded to form pellets, and then test pieces were molded from the pellets by injection molding at 270° C. The test pieces were irradiated with ultraviolet light for 500 hours in a Weather-O-Meter. Tensile strength before and after exposure was determined, and the percent tensile strength retained after the exposure is given in Table VI.

TABLE VI

| Ex. No. | Stabilizer | % Retention of Tensile Strength |
|---|---|---|
| Con- | Bis (2,2,6,6-tetramethyl-4-piperidinyl) sebacate | 56 |

TABLE VI-continued

| Ex. No. | Stabilizer | % Retention of Tensile Strength |
|---|---|---|
| Control 1 Control 2 | 2-hydroxy-4-octoxybenzophenone | 52 |
| 36. | [chemical structure] | 86 |
| 37. | [chemical structure] | 88 |
| 38. | [chemical structure] | 88 |
| 39. | [chemical structure] | 89 |
| 40. | [chemical structure] | 84 |

It is apparent that the stabilizers of the invention are effective ultraviolet light stabilizers for polybutylene terephthalate resins.

EXAMPLES 41 to 46

Polyurethane resin compositions were prepared using stabilizers of the invention and having the following formulation:

| Ingredient | Parts by Weight |
|---|---|
| Polyurethane resin (Asahi Denka U-100)[1] | 100 |
| Ca-stearate | 0.7 |
| Zn-stearate | 0.3 |
| 2,6-di-t-butyl-p-cresol | 0.1 |
| Octyldiphenylphosphite | 0.2 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for 5 minutes to form sheets 0.5 mm thick. Pieces 2.5 cm square were cut out from the sheets, and exposed to ultraviolet light in a Weather-O-Meter for thirty hours. At the conclusion of the test period, the color of the sheets was noted. The results are given in Table VII.

TABLE VII

| Ex. No. | Stabilizer | % Elongation Retention |
|---|---|---|
| Control 1 | 2,4-di-hydroxybenzophenone | 53 |

TABLE VII-continued

| Ex. No. | Stabilizer | % Elongation Retention |
|---|---|---|
| Control 2 | Bis (2,2,6,6-tetramethyl-4-piperidinyl) sebacate | 62 |
| 41. | [structure] | 77 |
| 42. | [structure] | 80 |
| 43. | [structure] | 79 |
| 44. | [structure] | 82 |
| 45. | [structure] | 80 |
| 46. | [structure] | 76 |

The stabilizers of the invention are clearly superior to the controls in enhancing resistance of the polyurethane resin to degradation under ultraviolet light.

Having regard to the foregoing disclosure, the following is claimed as the inventive and patentable embodiments thereof:

1. A 2,2,6,6-tetramethyl-4-piperidyl carbonic acid ester having the general formula:

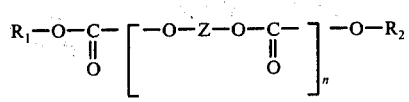

wherein:

$R_1$ and $R_2$ are selected from the group consisting of

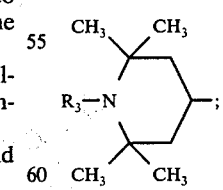

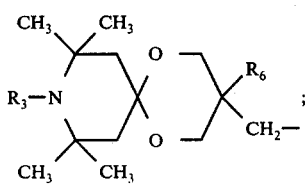

-continued

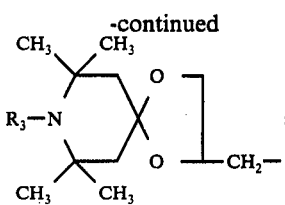
: and

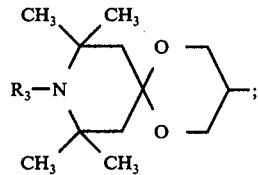

the $R_1$ and $R_2$ groups can be the same or different;

$R_3$ is selected from the group consisting of hydrogen and O·;

$R_6$ is lower alkyl;

$n$ is selected from the group consisting of 1, 2, 3, 4 and 5; and Z of —O—Z—O— is selected from the group consisting of bivalent aliphatic, cycloaliphatic, aromatic, mixed aliphatic-aromatic, aliphatic-cycloaliphatic and cycloaliphatic-aromatic radicals, and oxyalkylene radicals including ether —O— and thioalkylene radicals including thioether —S— linking groups between alkylene groups, having from one to about five oxy or thio groups and from two to about six alkylene groups having from two to about six carbon atoms.

2. A compound according to claim 1 in which $n$ is 1.
3. A compound according to claim 1 in which $n$ is 2.
4. A compound according to claim 1 in which $n$ is 3.
5. A compound according to claim 1 in which $R_3$ is hydrogen.
6. A compound according to claim 1 in which $R_3$ is O·
7. A compound according to claim 1 in which $R_6$ is methyl.
8. A compound according to claim 1 in which at least one of $R_1$ and $R_2$ is

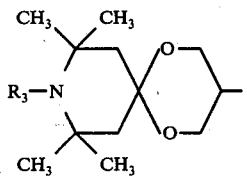

9. A compound according to claim 1 in which at least one of $R_1$ and $R_2$ is

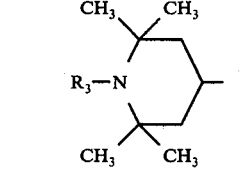

10. A compound according to claim 1 in which at least one of $R_1$ and $R_2$ is

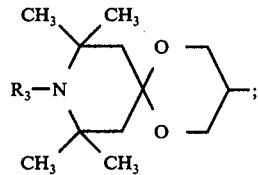

11. A compound according to claim 1 in which at least one of $R_1$ and $R_2$ is

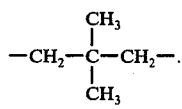

12. A compound according to claim 1 in which Z is alkylene having from two to about 24 carbon atoms.
13. A compound according to claim 12 in which Z is neopentylene $$-CH_2-\underset{\underset{CH_3}{|}}{\overset{\overset{CH_3}{|}}{C}}-CH_2-.$$

14. A compound according to claim 12 in which Z is hexylene.
15. A compound according to claim 1 in which Z is bis-(cycloalkylene) alkylidene having from fifteen to about twenty-four carbon atoms.
16. A compound according to claim 15 in which Z is bis-(cyclohexylene) isopropylidene.
17. A compound according to claim 1 in which Z is bis-(phenylene) alkylidene.
18. A compound according to claim 17 in which Z is bis-(phenylene) isopropylidene.
19. A compound according to claim 1 having the formula:

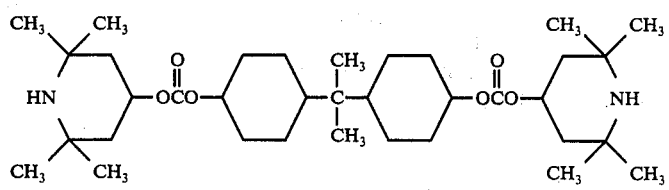

20. A compound according to claim 1 having the formula:

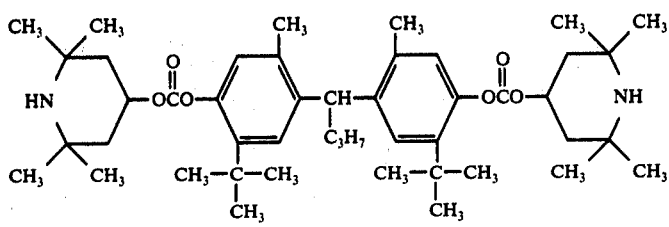

21. A compound according to claim 1 having the formula:

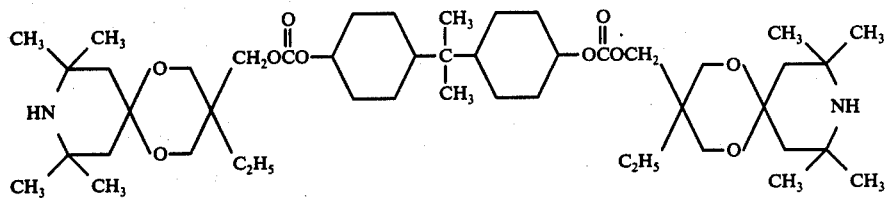

22. A compound according to claim 1 having the formula:

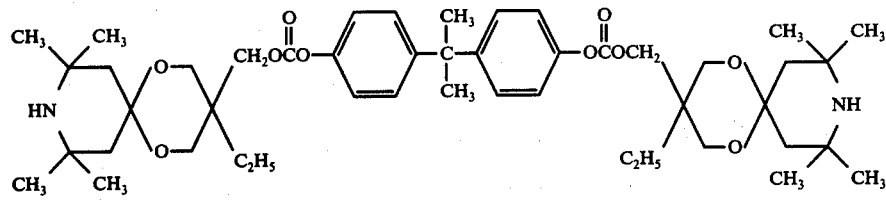

23. A compound according to claim 1 having the formula:

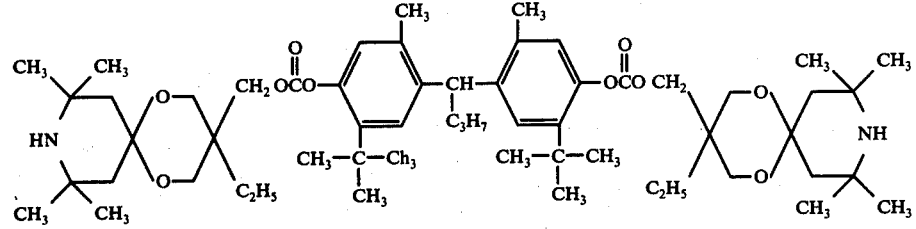

24. A polyvinyl chloride resin composition having improved resistance to deterioration when heated at 350° F., comprising a polyvinyl chloride resin and a compound in accordance with claim 1.

25. A polyvinyl chloride resin composition in accordance with claim 24, in which the polyvinyl chloride resin is polyvinyl chloride homopolymer.

26. A polyvinyl chloride resin composition in accordance with claim 24, in which the polyvinyl chloride resin in a copolymer of vinyl chloride and vinyl acetate.

27. An olefin polymer composition having improved resistance to deterioration comprising an olefin polymer selected from the group consisting of polymers of alpha-olefins having from two to six carbon atoms and polystyrene, and a compound in accordance with claim 1.

28. An olefin polymer composition in accordance with claim 27 wherein the polyolefin is polypropylene.

29. An olefin polymer composition in accordance with claim 27 wherein the polyolefin is polyethylene.

30. An acrylonitrile-butadiene-styrene polymer having its resistance to deterioration when heated at 300° F. and above enhanced by a compound in accordance with claim 1.

31. A polyester polymer composition having improved resistance to deterioration comprising a polyester polymer and a compound in accordance with claim 1.

32. A polyurethane resin composition having improved resistance to deterioration comprising a polyurethane resin and a compound in accordance with claim 1.

33. An ethylene-vinyl acetate copolymer composition having improved resistance to deterioration comprising an ethylene-vinyl acetate copolymer and a compound in accordance with claim 1.

* * * * *

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

[57] abstract, line 3 :

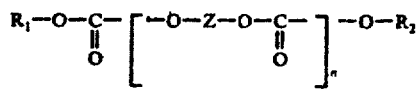

should be

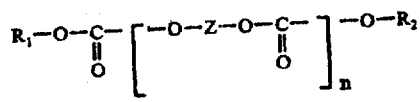

[57] abstract, line 27 : "O;" should be --O˙; --.
Column 8, line 24 : "r₁ and r₂" should be --R₁ and R₂--.
Column 8, line 26 : "O;" should be --O˙; --
Column 8, line 30 : " —O—Z—O—" should be —O—Z—O---.
Column 8, line 63 : "diemthylene" should be --dimethylene--
Column 9, Formula 1 :

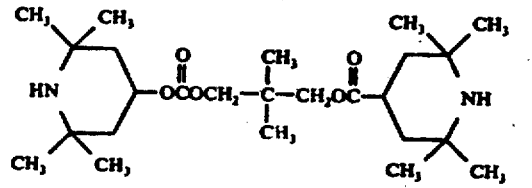

should be

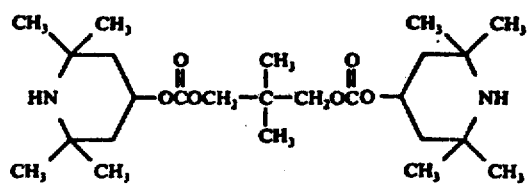

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 11, Formula 14 :

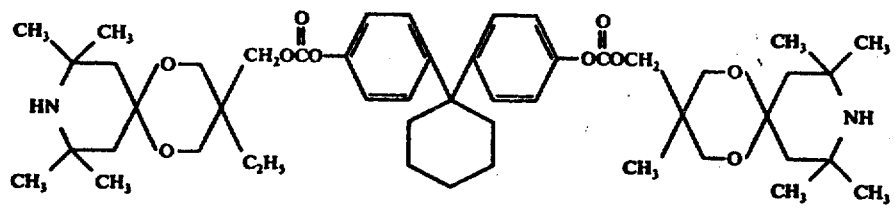

should be

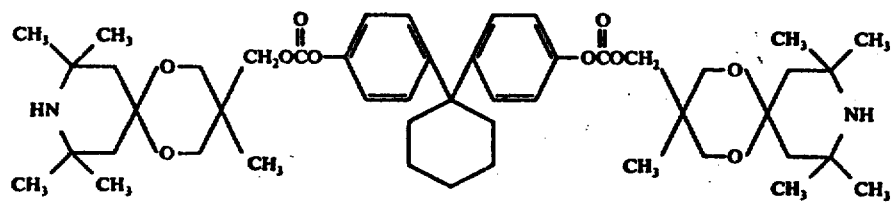

Column 13, Formula 24 :

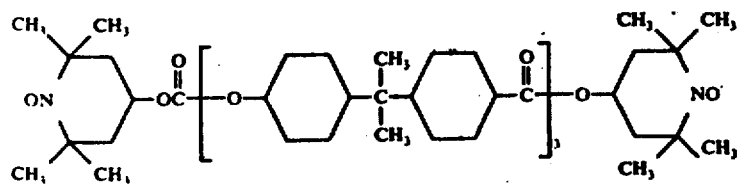

should be

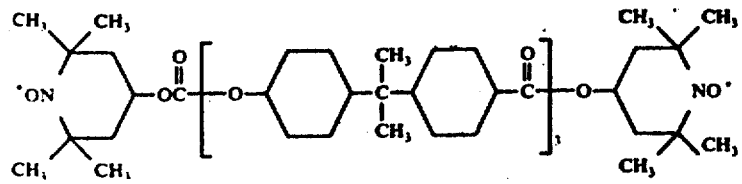

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 17, line 64 : "syntehsized" should be --synthesized--.
Column 19, line 45 should be

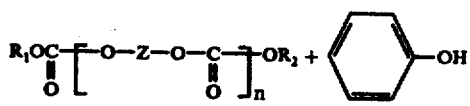

Column 21, line 45 : "polyepsiloncarprolactam" should be --polyepsiloncaprolactam--.
Column 22, line 15 : "orgaic" should be --organic--.
Column 25, Table II
under Example No. : "1" should be -- Control 1 --

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 26, Table II
Formula 11 :

11.

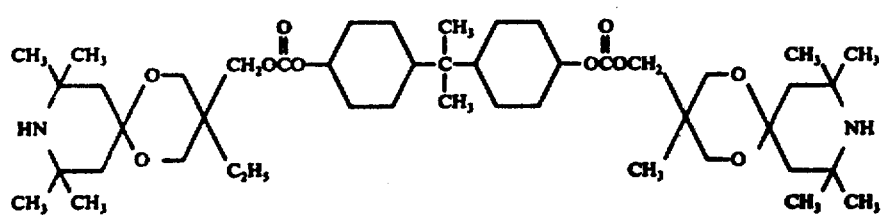

should be

11.

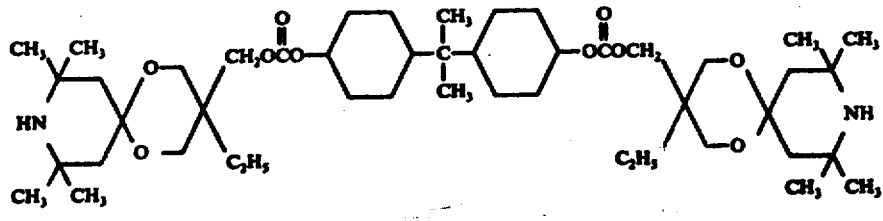

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 26, Table II
Formula 14 :

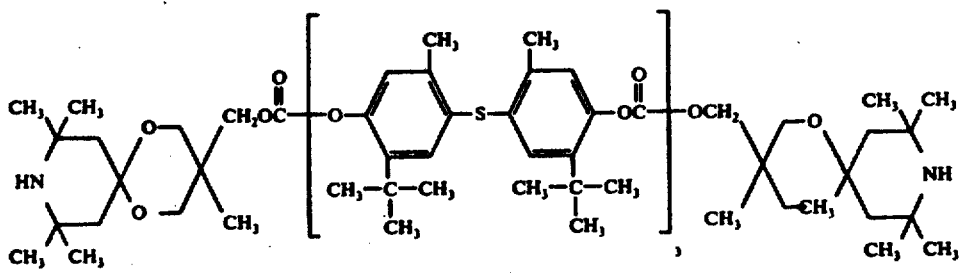

should be

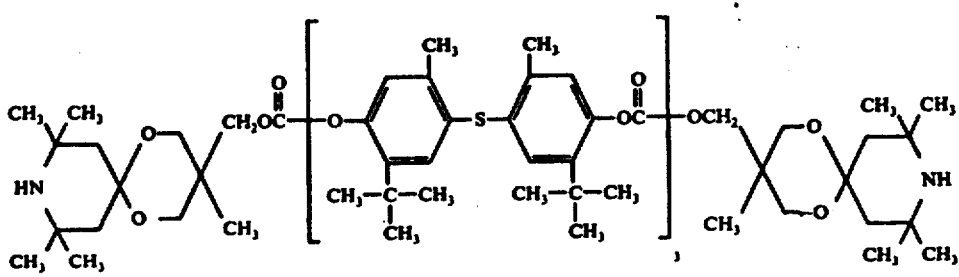

UNITED STATES PATENT AND TRADEMARK OFFICE
CERTIFICATE OF CORRECTION

PATENT NO. : 4,115,476

DATED : September 19, 1978

INVENTOR(S) : Motonobu Minagawa et al

It is certified that error appears in the above-identified patent and that said Letters Patent are hereby corrected as shown below:

Column 27, Table III,
Formula 17 :

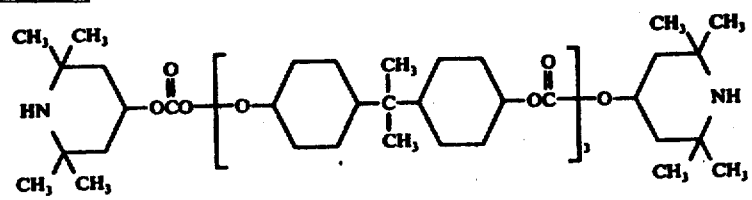

should be

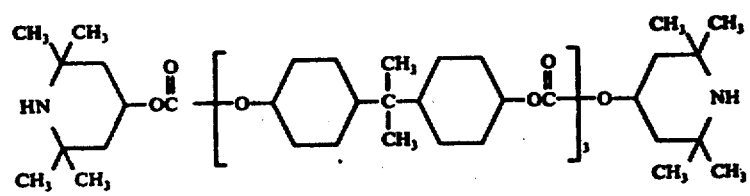

Column 27, Table III,
Formula 18 :

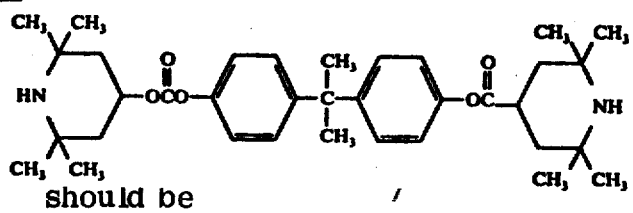

should be

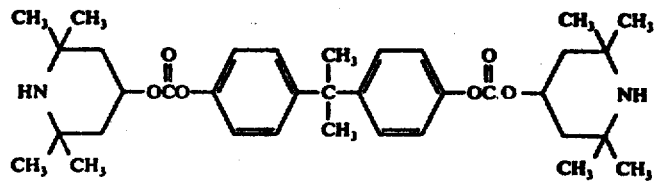

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 33, line 53 : after "chlorophenyl" please insert --)--.

Column 33, Table VI under Example No. : "Con" should be --Control 1--.

Column 35, Table VI under Example No. : please delete "trol 1".

Column 39, line 37 : "O.." should be --O·.--.

Column 41, line 45 :

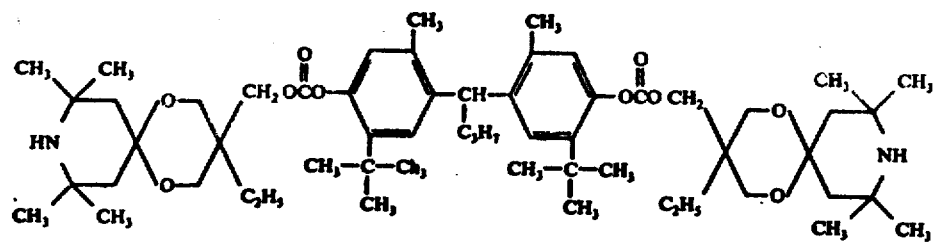

should be

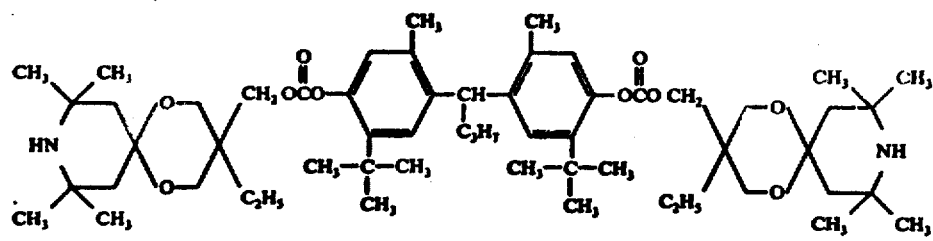

UNITED STATES PATENT AND TRADEMARK OFFICE
CERTIFICATE OF CORRECTION

PATENT NO. : 4,115,476
DATED : September 19, 1978
INVENTOR(S) : Motonobu Minagawa et al It is certified that error appears in the above-identified patent and that said Letters Patent are hereby corrected as shown below:

Column 41, line 60 : "in" should be --is--.

Signed and Sealed this

Eighth Day of January 1980

[SEAL]

Attest:

SIDNEY A. DIAMOND

Attesting Officer

Commissioner of Patents and Trademarks